United States Patent
Paul et al.

(10) Patent No.: US 10,533,977 B2
(45) Date of Patent: Jan. 14, 2020

(54) METHOD FOR DETECTING AND CHARACTERIZING DEFECTS IN A HETEROGENOUS MATERIAL VIA ULTRASOUND

(71) Applicant: ELECTRICITE DE FRANCE, Paris (FR)

(72) Inventors: Nicolas Paul, Montreuil (FR); Pierre-Louis Filiot, Paris (FR)

(73) Assignee: Electricite de France (FR)

( * ) Notice: Subject to any disclaimer, the term of this patent is extended or adjusted under 35 U.S.C. 154(b) by 289 days.

(21) Appl. No.: 15/529,414

(22) PCT Filed: Nov. 27, 2015

(86) PCT No.: PCT/FR2015/053245
§ 371 (c)(1),
(2) Date: May 24, 2017

(87) PCT Pub. No.: WO2016/083759
PCT Pub. Date: Jun. 2, 2016

(65) Prior Publication Data
US 2017/0328871 A1 Nov. 16, 2017

(30) Foreign Application Priority Data
Nov. 27, 2014 (FR) ...................... 14 61602

(51) Int. Cl.
*G01N 29/44* (2006.01)
*G01N 29/06* (2006.01)
(Continued)

(52) U.S. Cl.
CPC ....... *G01N 29/4463* (2013.01); *G01N 29/069* (2013.01); *G01N 29/11* (2013.01);
(Continued)

(58) Field of Classification Search
CPC .... G01N 29/069; G01N 29/11; G01N 29/265; G01N 29/4463; G01N 29/4472; G01N 29/449
(Continued)

(56) References Cited

U.S. PATENT DOCUMENTS 5,445,029 A * 8/1995 Falsetti .............. G01N 29/2487
73/602
6,484,584 B2 * 11/2002 Johnson ............... B23K 31/125
73/624
(Continued)

FOREIGN PATENT DOCUMENTS

EP 2778673 9/2014

OTHER PUBLICATIONS

International Search Report and Written Opinion, dated Mar. 10, 2016, application No. PCT/FR2015/053245.
(Continued)

*Primary Examiner* — John H Le
(74) *Attorney, Agent, or Firm* — Lerner, David, Littenberg, Krumholz & Mentlik, LLP

(57) ABSTRACT

A method for detecting and characterizing defects in a heterogeneous material via ultrasound. The method includes the following steps: emitting ultrasound waves from an emitting ultrasound transducer placed against the material; acquiring, using a receiving ultrasound transducer in various positions relative to the material, a plurality of time signals, representing the amplitude of the sound propagated in the material as a function of time, for a position of the receiving ultrasound transducer; determining a time function representing a spatially averaged power of the time signals that correspond to different positions of the receiving transducer; and—normalizing the time signals by the time function so as
(Continued)

to obtain normalized time signals. The defects in the material are detected from the normalized tune signal.

9 Claims, 5 Drawing Sheets

(51) Int. Cl.
*G01N 29/11* (2006.01)
*G01N 29/265* (2006.01)

(52) U.S. Cl.
CPC ......... *G01N 29/265* (2013.01); *G01N 29/449* (2013.01); *G01N 29/4472* (2013.01)

(58) Field of Classification Search
USPC ............. 702/35, 36, 39, 127, 150, 151, 159; 73/579, 602, 609, 620, 624, 627, 628, 73/632
See application file for complete search history.

(56) References Cited

U.S. PATENT DOCUMENTS

| | | | |
|---|---|---|---|
| 7,987,721 B2 * | 8/2011 | Schulz | G01N 29/11 73/620 |
| 8,656,782 B2 * | 2/2014 | Boehm | G01N 29/069 73/602 |
| 2007/0006651 A1 | 1/2007 | Kruger et al. | |

OTHER PUBLICATIONS

French Search Report, dated Sep. 25, 2015, French App No. 1461602, (Cover Sheet).

Sahimi, Muhammad, et al., "Propagation and localization of acoustic and elastic waves in heterogeneous materials: renormalization group analysis and numerical simulations", *Acta Mech*, vol. 205, Nos. 1-4, (Apr. 24, 2009), 197-222.

* cited by examiner

Angle (in probe increments)

Angle (in probe increments)

Angle (in probe increments)

Angle (in probe increments)

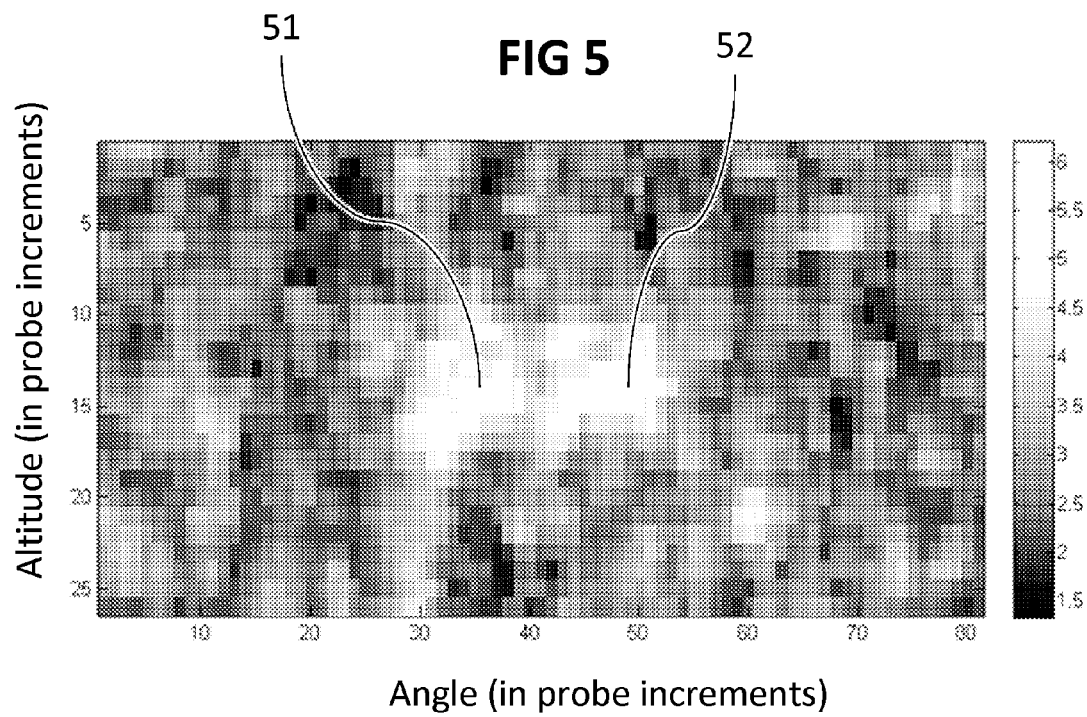
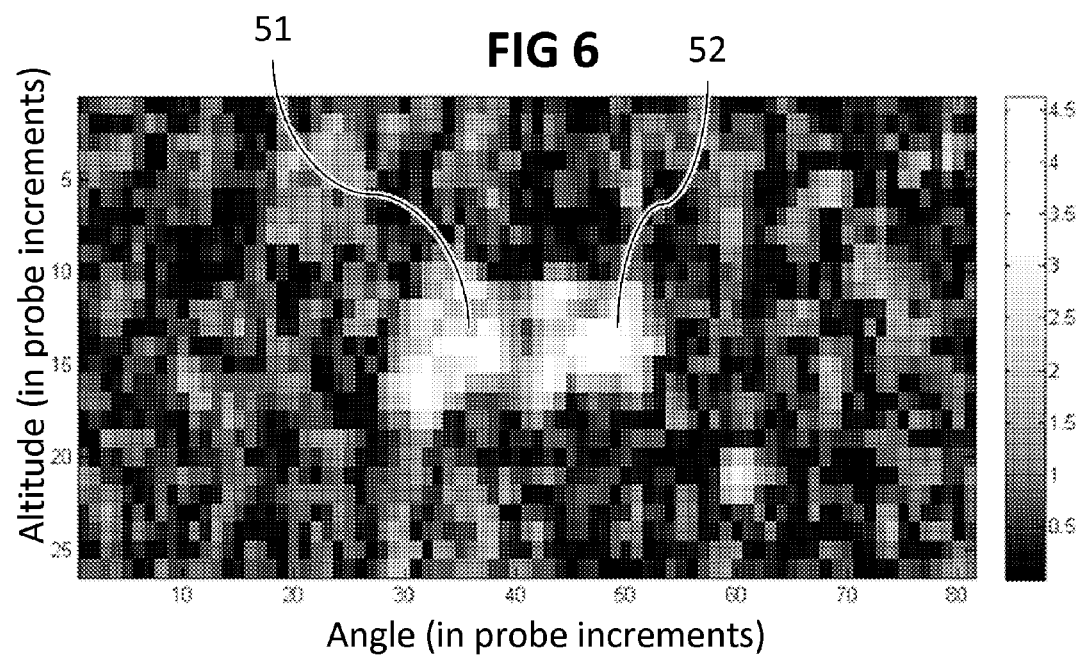

METHOD FOR DETECTING AND CHARACTERIZING DEFECTS IN A HETEROGENOUS MATERIAL VIA ULTRASOUND

GENERAL TECHNICAL FIELD AND BACKGROUND OF THE INVENTION

The present invention concerns the non-destructive testing of materials, and more precisely the detection and characterization of defects in a heterogeneous material by ultrasound.

Ultrasounds are commonly used for implementing non-destructive testing of materials. To do this, an ultrasound transducer is used, placed on the surface of the material to be examined, which emits ultrasonic waves into the material. These waves propagate through the material and are reflected by it according to its structure. The transducer receives these waves, and analysis of them makes it possible to detect any defects in the material.

However, for a heterogeneous material, i.e. a polycrystalline material with a grain size in the order of the ultrasonic wavelength in this material, the phenomenon of diffusion of the ultrasonic wave by the material structure becomes predominant. This diffusion can then lead to the generation of a structure noise, i.e. an ultrasonic signal of non-negligible amplitude received by the transducer and exhibiting characteristics similar to those that a wave reflected by a defect would transmit, thus leading to a deterioration of the ability to detect the defects actually present in the material.

Indeed, insofar as the structure noise has temporal and spectral characteristics similar to those of the defect signatures forming the useful signal, the conventional approaches for processing ultrasound signals, by time or frequency filtering, deconvolution or wavelet-based projection turn out to be ineffective.

The patent application US 2007/0006651 A1 describes a method for non-destructive testing by means of ultrasonic waves, based on the comparison of the amplitude of the frequency spectrum of a selected part of the signal with a reference amplitude. This application mentions the possibility of taking the measurements at different positions and describes the combination of these measurements to obtain a measurement signal that is an average in the spatial sense. However, such a method is not completely satisfactory, and the signal remains noisy.

OVERVIEW OF THE INVENTION

The present invention has the aim of proposing a method for detecting defects in a heterogeneous material by ultrasound that makes it possible to reduce the structure noise that affects the collected data.

For this purpose, a method is proposed for detecting and characterizing defects in a heterogeneous material by ultrasound, comprising the following steps:
- emission of ultrasounds from an ultrasound emitting transducer placed against the material,
- acquisition by an ultrasonic receiving transducer at different positions in relation to said material of a plurality of temporal signals representing the amplitude of the ultrasounds propagated in the material as a function of time for a position of the ultrasonic receiving transducer, the method comprising the steps of:
- determination of a temporal function representing a spatially-average power of the temporal signals corresponding to different positions of the ultrasonic receiving transducer, the temporal function representing the spatially-average power of the temporal signals being of the general formula:

$$f(t) = \left( \beta \sum_z |x(z,t) - m(t)|^\alpha \right)^\gamma$$

with $\alpha$, $\beta$ and $\gamma$ non-zero, $x(z,t)$ the temporal signal representing the amplitude of the sound propagated in the material as a function of time for a position z of the ultrasonic receiving transducer, and $m(t)$ a function of time,
- normalization of the temporal signals by means of said temporal function to obtain normalized temporal signals,
- detection and characterization of the defects of the material based on said normalized temporal signals.

The invention is advantageously completed by the following features, taken alone or in any of their technically possible combinations:
either $m(t)=0$, or $$m(t) = \frac{1}{N_z} \sum_z x(z,t),$$

or $m(t)=\text{median}_z\{x(z,t)\}$, and
either $\alpha=2$ and $\gamma=0.5$, or $\alpha=1$ and $\gamma=1$, and $$\beta \frac{1}{N_z} \text{ or } \beta = \frac{1}{N_z - 1} \text{ or } \beta = 1,$$

with $N_z$ the number of positions, $N_z$ being greater than 2;
let $m(t)=0$, $\alpha=2$, $\gamma=0.5$, $$\beta = \frac{1}{N_z},$$

the temporal function being a spatial standard deviation $\sigma(t)$ of the temporal signals of different positions of the receiving transducer, said positions being defined by their altitude h and their angle $\theta$:

$$\sigma(t) = \sqrt{\frac{1}{N_h N_\theta} \sum_{N_h} \sum_{N_\theta} x^2(h, \theta, t)}$$

the normalization of a temporal signal $x(z,t)$ by means of said temporal function $f(t)$ corresponds to the division of said temporal signal by said temporal function:

$$x_{norm}(z,t) = \frac{x(z,t)}{f(t)}$$

a temporal signal representing the amplitude of the sound propagated in the material as a function of time for a position of the receiving transducer is a A-type spatiotemporal representation representing the amplitude of the sound propagated in the material as a function of time for a position of the receiving transducer;

the detection of the defects comprises a step of determination of at least one C-type spatial representation by selecting for each position of the ultrasonic receiving transducer the maximum value over time of the absolute value of the normalized temporal signal corresponding to this position;

the detection of the defects comprises a step of spatial filtering of said at least one C-type spatial representation by means of a low-pass spatial filter;

the detection of the defects comprises a step of comparison with a detection threshold of the ratio of, on the one hand, the absolute value of the difference between the value taken by the C-type spatial representation for a position and the average of the values of the C-type spatial representation and on the other hand the standard deviation of the values of the C-type spatial representation;

prior to the determination of the temporal function:

at least one C-type spatial representation is determined by selecting for each ultrasonic receiving transducer position the maximum value over time of the absolute value of the temporal signal corresponding to this position, a pre-processing bi-dimensional low-pass spatial filter is applied to this C-type spatial representation in order to obtain an average level of the structure noise at each measurement position, each temporal signal is divided by the average level of the structure noise at the measurement position with which said temporal signal is associated.

The invention also relates to a computer program product comprising program code instructions for executing the method according to the invention when said program is executed on a computer.

OVERVIEW OF THE FIGURES

The invention will be better understood thanks to the description below, which relates to a preferred embodiment, given by way of non-limiting example and explained with reference to the appended schematic drawings, wherein.

Figure 4:
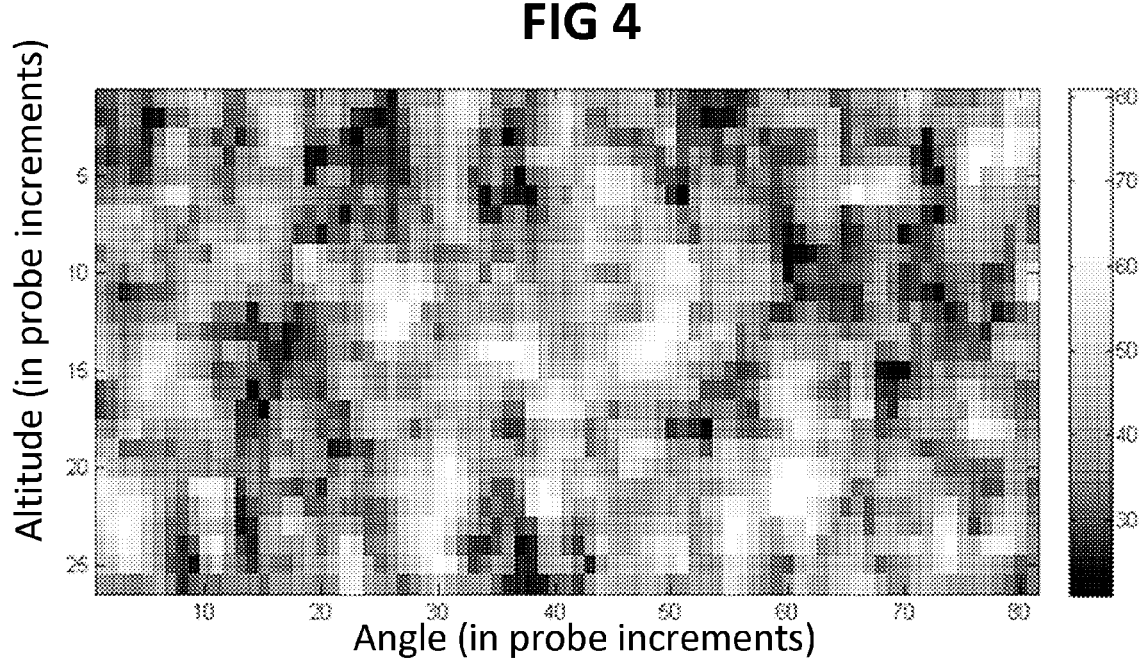
FIG. 4 is an example of C-type representation corresponding to the selection, for each position of the ultrasonic receiving transducer, of the maximum value over time of the absolute value of the temporal signal corresponding to this position, before normalization.

FIG. 5 illustrates the C-type representation of FIG. 4 after normalization by means of the spatial standard deviation of the temporal signals, FIG. 6 illustrates a C-type representation of the ratio of, on the one hand, the absolute value of the difference between the value of the C-type representation of FIG. 5 and the average of these values, and, on the other hand, the standard deviation of the values of the C-type representation of FIG. 5.

DETAILED DESCRIPTION

For illustration purposes, the following description will be made in the context of non-destructive testing of tubes for penetrating the bottom surface of a vessel of a nuclear reactor by means of ultrasonic transducers. Such a way of acquiring the transducer measurements is currently carried out, particularly to implement the technique of so-called Time of Flight Diffraction (TOFD), the acquisition protocol of which can be employed for the present invention.

The inspection of tubes for penetrating the bottom surface of a vessel of a nuclear reactor is subject to several constraints specific to the nuclear sector. Firstly, this environment is liable to cause premature ageing of materials, and secondly the consequences of a structural failure are such that any defects should be detected as soon as possible. Moreover, the accessibility of these penetration tubes is restricted to their interior, which makes it necessary to inspect the whole thickness of the tube from its internal face, since an inspection from the exterior of the tubes is hard to envision.

A tube for penetrating the bottom surface of a vessel is typically made of Inconel, i.e. an alloy mainly based on nickel, chrome, and iron, and also containing copper, manganesium and molybdenum, and optionally other components, generally in lesser quantity. It is a heterogeneous material, with a structure having grains of a size comparable to the wavelength of the ultrasonic waves employed in non-destructive testing. By way of example, the frequency of the ultrasonic waves generally used in non-destructive testing can range from 0.1 to 50 MHz, the 2-10 MHz band being the most often used. The wavelength, in this band, is thus for practical purposes between 3 mm and 0.5 mm for metals such as steel or aluminum. Note that the method is not necessarily restricted to a heterogeneous material, but has an advantageous application therein.

The inspection of such tubes is generally done by means of two types of probe. One of the probes is suitable for detecting longitudinal defects, and gives a so-called TOFD-L longitudinal signal, whereas the other of the probes is suitable for detecting circumference defects, which gives a so-called TOFD-C circumferential signal. The two probes can for example sweep the internal surface of the tube in a helical manner.

Figure 1A:
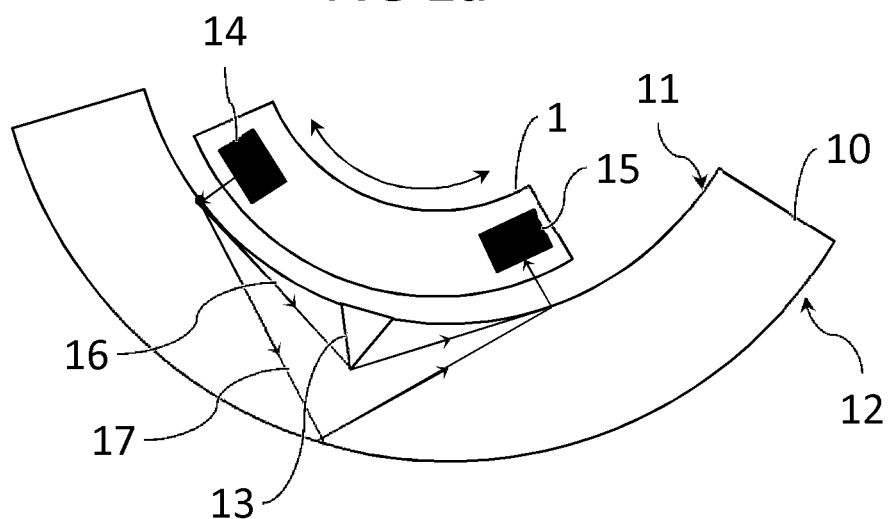
FIGS. 1a and 1b illustrate the inspection of a tube by a probe, dedicated to the detection of longitudinal and circumferential defects respectively.
Figure 1B:
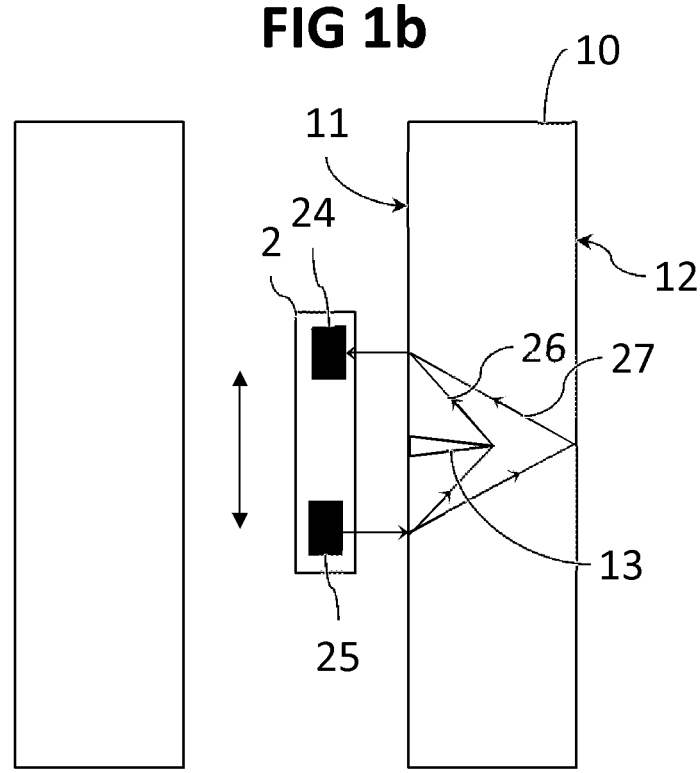

FIGS. 1a and 1b illustrate the scanning of a tube 10 by the two types of ultrasonic probe. FIG. 1a thus shows a probe 1 of TOFD-L (longitudinal) type inspecting a tube 10, arranged facing the internal wall 11 of this tube 10, the curve of which is followed by the probe 1. The tube 10 has a defect 13, presented here in the form of a notch. The emitting transducer 14 and the receiving transducer 15 of the probe 1 are arranged so as to be oriented in relation to the other perpendicularly to the longitudinal axis of the tube 10. They are therefore located in a plane perpendicular to said longitudinal axis of the tube 10.

FIG. 1b shows a probe 2 of TOFD-C (circumferential) type inspecting the tube 10, having the defect 13. The TOFD-C 2 probe is arranged facing the internal wall 11 of this tube 10, the curve of which it follows. The emitting transducer 24 and the receiving transducer 25 of the TOFD-C probe 2 are arranged so as to be aligned in the longitudinal axis of the tube 10. They are therefore located in a plane parallel to said longitudinal axis of the tube 10.

For both probe types, the measurement method is similar, as is the detection method that will be described. It is therefore possible to use one type of probe or the other, or else both. Ultrasounds are emitted from the ultrasonic emitting transducer 14, 24 placed against the material. The probe sweeps the tube, and, for a plurality of positions identified by the altitude h and the angle θ, a shot of ultrasonic waves is fired, and the reflected signal is received by the ultrasonic receiving transducer 15, 25. For example, for the measurements, the altitude increment can be of 0.5 mm, and the rotation increment of 1.44°.

The data thus acquired are defined by an amplitude as a function of time related to an altitude h and an angle θ. We will write z the position defined by an altitude h and an angle θ. We will therefore write:

$x_L(h, \theta, t)$ or $x_L(z, t)$: the temporal signals received by the TOFD-L 1 probe, and $x_C(h, \theta, t)$ or $x_C(z, t)$: the temporal signals received by the TOFD-C 2 probe.

From this data, several types of representation can be constructed:

the representation A, or A-scan, which is a temporal signal for a probe position, the data of which is written $x_{L\ or\ C(h,\ \theta)}(t)$ or $X_{L\ or\ L(z)}(T)$;

the representation B, or B-scan, which can be either:

a signal in two dimensions, angle/time, for a given altitude: $x_{L\ or\ C(h)}(\theta, t)$, or a signal in two dimensions, angle/time, for a given angle: $x_{L\ or\ C(\theta)}(h, t)$;

the representation C, or C-scan, which is a signal in two dimensions corresponding to the maximum amplitudes (in absolute value) measured for each position of the probe $$y_{L\ or\ C}(h, \theta) = \max_t |x_{L\ or\ C}(h, \theta, t)| \text{ or}$$

$$y_{L\ or\ C}(z) = \max_t |x_{L\ or\ C}(z, t)|$$

For more convenience, and insofar as they are equivalent, in the remaining text, the indices (L or C), concerning the longitudinal or circumferential aspect of the probe that has acquired the signals being studied, will be omitted.

Figure 3A:
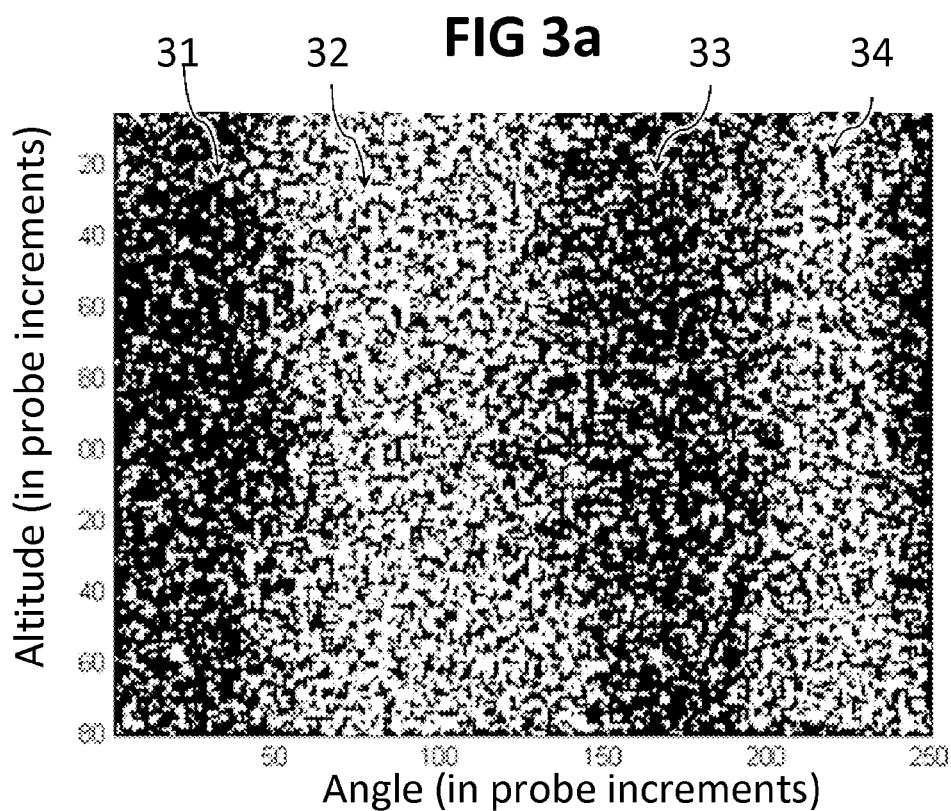
FIGS. 3a, 3b and 3c are examples of C-type representations illustrating various pre-processing steps for reducing the spatial variability of the structure noise.

Preferably, before continuing the method, pre-processing is employed in order to reduce the spatial variability of the structure noise and thus improve the effectiveness of subsequent processing. For this purpose, we first determine at least one C-type spatial representation by selecting, for each position of the ultrasonic receiving transducer, the maximum value over time of the absolute value of the temporal signal corresponding to this position, as indicated above. FIG. 3a illustrates a C-type representation, or C-scan, with the vertical axis representing the altitude, expressed here in probe increments of 0.5 mm, and the horizontal axis the angles θ, expressed here in angular increments of 1.44°. In this FIG. 3a, as well as the following FIGS. 3b and 3c, a dark color indicates a low value, while a light color indicates a high value. We can distinguish between at least four zones distinguishable from one another by their average level: a first zone 31 corresponding to the angles between 0 and approximately 50 angular increments of the probe has a low average value (dark color), a second zone 32 corresponding to the angles between approximately 50 angular increments and approximately 150 angular increments has a high average level (light color), a third zone 33 corresponding to the angles between approximately 150 angular increments and approximately 200 angular increments has a low average level (dark color), a fourth zone 34 corresponding to the angles between approximately 200 angular increments and approximately 250 angular increments has a high average level (light color).

A pre-processing two-dimensional low-pass spatial filter is applied to this C-type spatial representation in order to obtain an average level of structure noise at each measurement position. The two cut-off frequencies, one for altitude h and the other for angle θ, are chosen to correspond to the inverse of the distance after which the level of structure noise is supposed to be relatively constant. Taking the example above, this gives a cut-off frequency and 1/50 probe increments or 1/72 degrees$^{-1}$.

Figure 3B:
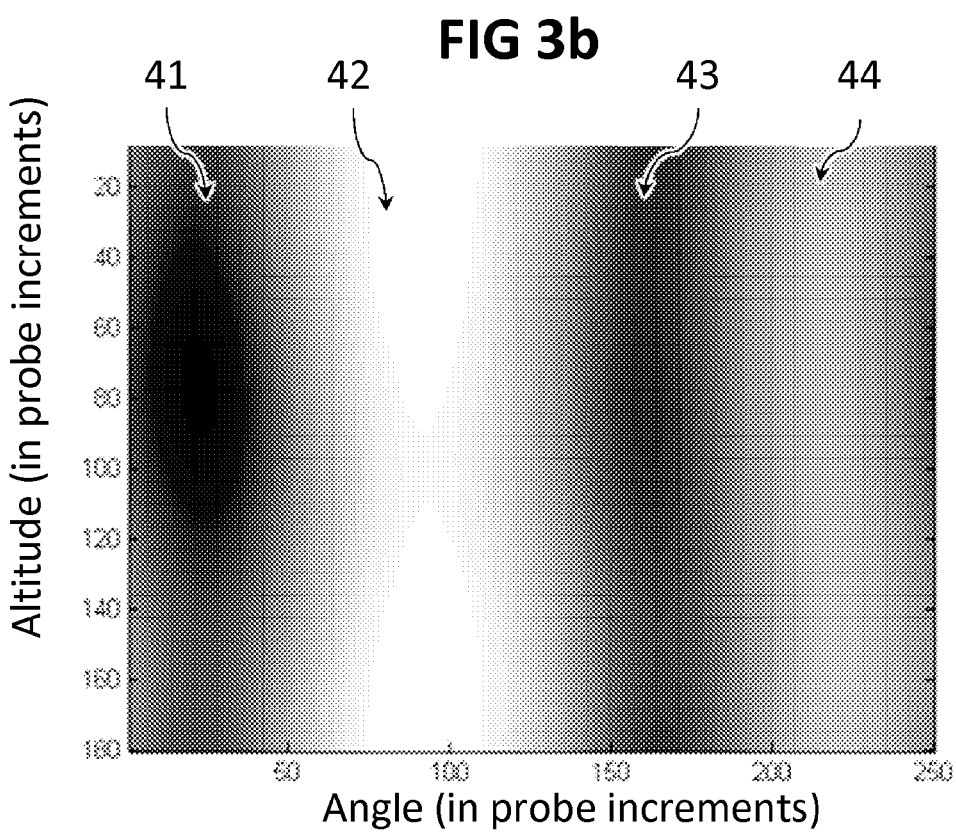
Figure 3C:
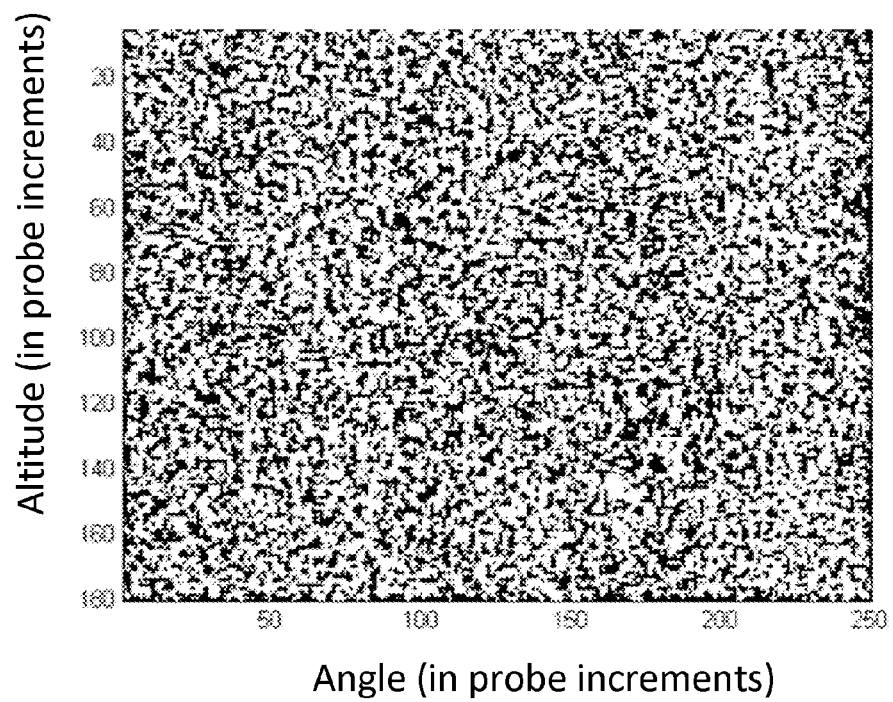

FIG. 3b illustrates the image of the average structure noise values corresponding to the C-scan of FIG. 3a after its filtering by a pre-processing two-dimensional low-pass spatial filter. Here the four zones distinguishable from one another by their average level can be seen: a first zone 41 corresponding to angles between 0 and approximately 50 angular increments has a low average value (dark color), a second zone 42 corresponding to angles between approximately 50 angular increments and approximately 150 angular increments has a high average value (light color), a third zone 43 corresponding to angles between approximately 150 angular increments and approximately 200 angular increments has a low average value (dark color), a fourth zone 44 corresponding to angles between approximately 200 angular increments and approximately 250 angular increments has a high average value (light color).

The average level of structure noise at each measurement position is thus obtained. Each temporal signal, i.e. each A-scan, is then divided by the average level of structure noise at the measurement position with which said temporal signal is associated. By writing P(z) the average level of structure noise at the measurement position z, and taking the notation of the A-scans indicated above, this gives for the A-scans thus pre-processed:

$$x_{(z)}(t)_{pre-processed} = \frac{x_{(z)}(t)}{P(z)}$$

After this optional pre-processing of the spatial variability of the structure noise in the A-scans, the temporal variability of the structure noise in the A-scans can now be addressed. A-type representations correspond to a plurality of temporal signals representing the amplitude of the sound propagated through the material as a function of time for a position of the ultrasonic transducer 15, 25. It is on the basis of these temporal signals that the defect detection will be implemented.

In FIGS. 1a and 1b, various trajectories of ultrasonic waves are represented. The ultrasonic waves are emitted by the emitting transducer 14, 24 and penetrate the tube 10 at its inner wall 11, then propagate through the material of said tube 10. A first trajectory 16, 26 constitutes a short path for the ultrasonic waves, which are diffracted by the defect 13 in the direction of the receiving transducer 15, 25. A second trajectory 17, 27 constitutes a long path for the ultrasonic waves, which are reflected by the outer wall 12 of the tube 10 in the direction of the receiving transducer 15, 25.

Various trajectories are thus possible for the ultrasonic waves received by the receiving transducer 15, 25, from which the different measurement signals (A-scan, B-scan or C-scan) are constructed. However, the longer the trajectory of the ultrasonic wave, the greater the interactions with the grains of the material. This manifests as a structure noise power that increases with the time of flight of the waves, and thus with the reception time thereof.

To characterize this phenomenon, we determine a temporal function representing the spatially-average power of the temporal signals corresponding to different positions of the receiving transducer against the material as a function of the propagation time of said signals. The term "spatially-average power" is understood to mean the average in space, i.e. along z or (h,θ) of a magnitude, in this instance the instantaneous power, at a given instant t. The temporal function is representing this spatially-average power, which means that it can be directly or indirectly related to the spatially-average power, and consequently be based on a magnitude not equivalent to this spatially-average power, but related thereto, such as the spatial standard deviation. In all cases, this temporal function involves, for each instant t, a sum over the space taking into account the values taken by the temporal signals over said space at this instant t.

It should be noted that it is indeed the power that is spatially-averaged, and not the measurement signal. Thus, the temporal function in question is a time-dependent signal, which at an instant t takes a value representing the average of the powers at this instant t of the temporal signals corresponding to different positions of the ultrasonic receiving transducer.

This temporal function has the general formula:

$$f(t) = \left(\beta \sum_z |x(z,t) - m(t)|^\alpha\right)^\gamma$$

with $\alpha$, $\beta$ and $\gamma$ non-zero, $x(z,t)$ the temporal signal representing the amplitude of the sound propagated in the material as a function of time for a position z (defined by the altitude and the angle) of the ultrasonic receiving transducer, t being the time of flight or of propagation of the ultrasonic wave, and m(t) a temporal function.

We can choose:
either m(t)=0, or $$m(t) = \frac{1}{N_z} \sum_z x(z,t),$$

i.e. the average of the signal x over space, or $m(t)=\text{median}_z\{x(z,t)\}$, and
preferably either $\alpha=2$ and $\gamma=0.5$, which corresponds to the standard deviation, or $\alpha=1$ and $\gamma=1$, which corresponds to the average absolute deviation, and
preferably $$\beta = \frac{1}{N_z} \text{ or } \beta = \frac{1}{N_z - 1} \text{ or } \beta = 1,$$

with $N_z$ the number of positions taken into account, greater than two.

Thus, taking m(t)=0, $\alpha=2$, $\gamma=0.5$, $$\beta = \frac{1}{N_z},$$

the temporal function is a spatial standard deviation σ(t) of the temporal signals of different positions of the receiving transducer, said positions being defined by their altitude h and their angle θ:

$$\sigma(t) = \sqrt{\frac{1}{N_h N_\theta} \sum_{N_h} \sum_{N_\theta} x^2(h, \theta, t)}$$

Preferably, the different positions of the receiving transducer from which the temporal function is determined correspond to a portion of the studied material, and not its entirety. A temporal function is therefore determined for each of these material portions. The material portions thus processed can be juxtaposed, as in the case of block processing, but preferably, the material portions lie on top of one another and are each centered on a measurement position, such that there is a temporal function for each measurement position that is determined from the zone surrounding said position on the material.

The extent of the portion of material taken into account depends on the spatial variability of the structure noise, and therefore the spatial variability of the power of the measured signals. By way of example, the zone surrounding said position can extend from 100 measurement points, or positions, in height, and 100 measurement points in angle. With a measurement increment in height of 0.5 mm and an angular increment of 1.44 degrees, we thus obtain a material portion extending from 50 mm in height and from 150 degrees in width.

Figure 2A:
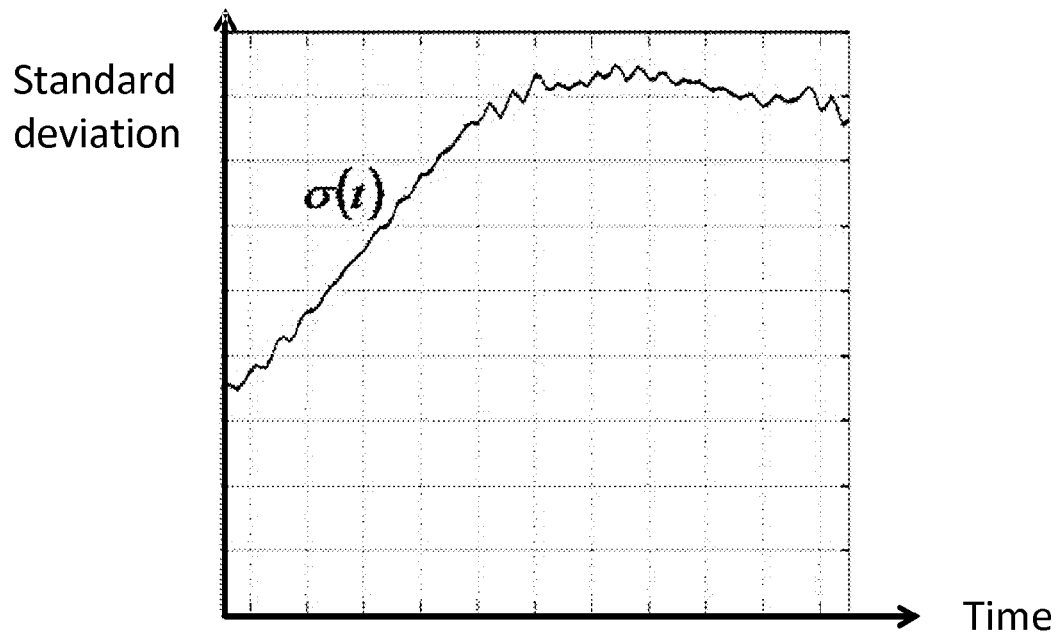
FIG. 2 illustrates the variation of the standard deviation of the structure noise as a function of the arrival time.
Figure 2B:
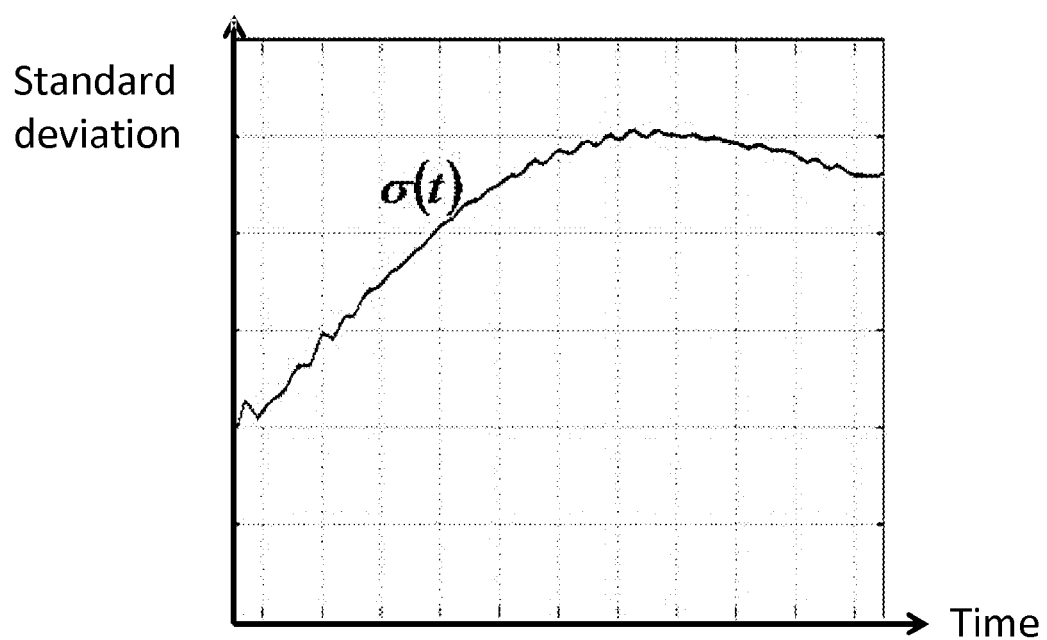

FIGS. 2a and 2b illustrate the spatial standard deviation of the temporal signals as a function of the arrival time for the probe L (FIG. 2a) and the probe C (FIG. 2b) for a position on the surface of a tube 10. Since the tube 10 contains only few defects, the temporal variation of the standard deviation is essentially due to structure noise. It is observed that the standard deviation increases with the arrival time of the signal, at least at first, and therefore with the time between the emission of the ultrasounds and their reception by the probe affects the power of the structure noise.

This is because, as explained above, for a short flight time of an ultrasonic wave, few diffusion paths are possible. On the other hand, for a long flight time there are many different corresponding diffusion paths for the ultrasonic wave to take. The total received signal being the sum of the diffused ultrasonic waves, the received power will be for the long flight times, and this in spite of the greater attenuation of each diffusion. The attenuation of the signals is however observed on the longer flight times, as is their dispersion represented by the standard deviation, as shown in the slight final decrease of the curves of FIGS. 2a and 2b.

The temporal function representing the spatially-average power of the temporal signals is then used to normalize the temporal signals. More precisely, the amplitude of a temporal signal x(z,t) is divided by the temporal function f(t):

$$x_{norm}(z, t) = \frac{x(z, t)}{f(t)}$$

Thus, when the temporal function used is the standard deviation σ(t), it is possible to normalize the A-scan signals, which are temporal signals for a probe position, the data of which are written $x_{(h, \theta)}(t)$, omitting the index L or C indicating the type of defect sought by the probe.

$$x_{(h,\theta)}^{norm}(t) = \frac{x_{(h,\theta)}(t)}{\sigma(t)}$$

The normalization makes it possible to increase the contrast between the useful signal due to any defect in the material and structure noise. It is then possible to construct normalized B-scans from these normalized A-scans. It is also possible to construct normalized C-scans from these normalized A-scans, by selecting for each position of the ultrasonic receiving transducer the maximum value over time of the normalized temporal signal corresponding to this position:

$$y^{norm}(h, \theta) = \max_t \left| \frac{x_{(h,\theta)}(t)}{\sigma(t)} \right|, \text{ or}$$

$$y^{norm}(z) = \max_t \left| \frac{x_{(z)}(t)}{\sigma(t)} \right|$$

A signal is thus obtained that is derived from the normalization of the temporal signals by the temporal function representing the spatially-average power of the temporal signals, in this instance by the standard deviation in this example.

FIGS. 4 and 5 illustrate the implementation of the normalization on an example of a C-type representation, i.e. a C-scan, corresponding to the selection, for each position of the ultrasonic receiving transducer, of the maximum value over time of the absolute value of the temporal signal corresponding to this position. As previously, the vertical axis represents the altitude, expressed here in probe increments of 0.5 mm, and the horizontal axis the angles, expressed here in angular increments of 1.44°. In this FIG. 4, and also in FIG. 5, a dark color indicates a low value, while a light color indicates a high value.

FIG. 4 is therefore an example of a C-scan, before this normalization. A distribution of values, visible by their color, is observed that appears random. On the other hand, in FIG. 5, which illustrates the C-type representation of FIG. 4 after normalization by means of the spatial standard deviation of the temporal signals with a shape similar to that of FIGS. 2a and 2b, two sets 51 and 52 which are distinguished by higher values than the surrounding area are highlighted in the center of the C-scan. We have thus highlighted the presence of two defects corresponding to these two sets.

It is still necessary to detect and characterize the defects by detecting their signature in the derived signal. In this regard, the detection and characterization of the defects is preferably carried out by means of a two-dimensional spatial signal such as the C-scan, rather than a temporal signal or a space-temporal signal such as a B-scan. Specifically, whatever the profile of the defect, for example whether it is a rectangular or semi-elliptic notch, the projection of the defect on the C-scan is a straight line segment, vertical for a longitudinal notch or horizontal for a circumferential notch, or else a combination of the two, for example as in the case of a crack extending diagonally, at once circumferentially and longitudinally in the tube. The use of a C-type spatial representation, in two spatial dimensions, thus makes it possible to be independent of the profile of the defects to be detected.

Defects such as notches can extend over several tens of millimeters. The points of the C-scan at this signature are therefore mutually intercorrelated, i.e. they exhibit coherence over several spatially adjacent positions at the defect. On the other hand, in the absence of a defect signature in the C-scan, with only noise, the C-scan exhibits a much weaker intercorrelation around any point. Thus, each notch can be identified by a spatial persistence on the C-scan following the angle and/or the altitude where it appears.

Furthermore, the configuration of the TOFD probes, of C type or L type, also leads to spatial persistence. Specifically, the ultrasonic signal received is affected by the defect as long as the latter is located between the emitting transducer 14, 24 and the receiving transducer 15, 25 (see FIGS. 1a and 1b). As a consequence, the persistence of the defect can be observed at several positions (altitudes, angles) in the vicinity of a defect on the C-scan.

This spatial coherence is therefore made use of to highlight the useful signal representing the defects at the expense of the noise, less spatially correlated. A spatial filter making use of this spatial correlation is therefore implemented on the signal derived from the normalization, by applying a low-pass spatial filter to the C-scan in order to filter it spatially. The low-pass spatial filter is designed to attenuate the variability of the structure noise, characterized by the spatial standard deviation of the distribution of its amplitudes, while preserving the level of the signature of a defect.

The filter is known as spatial as it does not involve any temporal considerations, the C-scan being a purely spatial signal, without temporal variable. The spatial filter can be a one-dimensional filter applied to the angular component $\theta$, i.e. for each altitude h the normalized signal $y_{(h)}^{norm}(\theta)$ is filtered, and/or on the signal of altitude h, i.e. for each altitude h the normalized signal $y_{(\theta)}^{norm}(h)$ is filtered.

The spatial cut-off frequency of the low-pass spatial filter can be chosen as a function of the minimum size $\Delta L_{min}$ of the defects that we are seeking to detect, as being the inverse of this minimum size $\Delta L_{min}$. Thus, to detect defects of at least 10 mm, the spatial cut-off frequency is therefore chosen as being less than 100 m$^{-1}$. The spatial filter is typically a Butterworth filter.

The spatial filter can also be a two-dimensional low-pass spatial filter applied to the C-scan image. The frequency response in two dimensions can be chosen according to the minimum size of the sought—for detects, in the same way as for a one-dimensional spatial filter.

The C-scan thus filtered makes it possible to obtain a defect detection map. Specifically, the signature appears on the C-scan, particularly as an amplitude different from the surroundings, which makes it possible to detect them, but also to locate them. This is because a C-scan is a spatial representation, and each point is located by its altitude and its angle.

A simple detection method consists in using a given threshold: any exceeding of the threshold by a set of adjacent points of the C-scan signals the presence of a defect.

A slightly more elaborate detection method is based not on the values directly taken by the C-scan, $y^{filtered}(z)$, but on comparison with a detection threshold of the ratio of, on the one hand, the absolute value of the difference between the value taken by the C-type spatial representation for a position and the average of the values of the C-type spatial representation, and on the other hand, the standard deviation of the values of the C-type spatial representation. Using the previous notation, this gives:

$$\frac{|y^{filtered}(z) - \text{average}|}{\gamma} > \text{threshold}$$

with $y^{filtered}(z)$ the value of the C-scan, optionally filtered, taken at the position z, average the spatial average of the C-scan, and γ the standard deviation of the values of the C-scan. The detection threshold can for example be 3.

This method makes it possible to highlight defects even more clearly. For illustration purposes, FIG. 6 illustrates the implementation of this calculation, without the spatial filtering step mentioned previously being implemented, for reasons of simplicity of demonstration. FIG. 6 thus shows a C-scan corresponding to the ratio of, on the one hand, the absolute value of the difference between the value of the C-type representation of FIG. 5 and of the average of these values, and on the other hand, the standard deviation of the values of the C-type representation of FIG. 5. The two sets 51 and 52 of high values can be seen again here, but highlighted in relation to the zones surrounding them, with values 3 to 4 times higher than them. It is then easy to locate the defects.

Once the defect is located in altitude and in angle, the position of the amplitude peak on the normalized A-scan corresponding to the position of the located defect makes it possible to determine the depth of the defect.

The method described is typically implemented by a computer provided with a processor and a memory. For this purpose, provision is made for a computer program product comprising program code instructions for executing the method according to the invention when said program is executed on a computer.

The invention is not limited to the embodiment described and represented in the appended figures. Modifications remain possible, particularly as regards the composition of the various elements, or modifications by substitution of technical equivalents, without however departing from the scope of protection of the invention.

The invention claimed is:

1. A method for detecting and characterizing defects in a heterogeneous material by ultrasound, comprising the following steps:
    emission of ultrasounds from an ultrasonic emitting transducer placed against the material,
    acquisition by an ultrasonic receiving transducer at different positions in relation to said material of a plurality of temporal signals representing the amplitude of the ultrasounds propagated in the material as a function of time for a position of the ultrasonic receiving transducer,
characterized in that the method comprises the steps of:
    determination of a temporal function representing a spatially-average power of the temporal signals corresponding to different positions of the ultrasonic receiving transducer, the temporal function representing the spatially-average power of the temporal signals being of the general formula:

$$f(t) \left( \beta \sum_z |x(z, t) \; m(t)|^\alpha \right)^\gamma$$

with $\alpha$, $\beta$ and $\gamma$ non-zero numbers, $x(z,t)$ the temporal signal representing the amplitude of the sound propagated in the material as a function of time for a position z of the ultrasonic receiving transducer, and m(t) a function of time,
    normalization of the temporal signals by means of said temporal function to obtain normalized temporal signals,
    detection and characterization of the defects of the material based on said normalized temporal signals.

2. The method as claimed in claim 1, wherein:
either m(t)=0, or $$m(t) = \frac{1}{N_z} \sum_z x(z, t),$$

or m(t)=median$_z$[x(z,t)], and
either $\alpha$=2 and $\gamma$=0.5, or $\alpha$=1 and $\gamma$=1, and $$\beta = \frac{1}{N_z} \text{ or } \beta = \frac{1}{N_z - 1} \text{ or } \beta = 1,$$

with $N_z$ the number of positions, $N_z$ being greater than 2.

3. The method as claimed in claim 2, wherein m(t)=0, $\alpha$=2, $\gamma$=0.5, $$\beta = \frac{1}{N_x},$$

the temporal function being a spatial standard deviation σ(t) of the temporal signals of different positions of the receiving transducer, said positions being defined by their altitude h and their angle θ:

$$\sigma(t) \sqrt{\frac{1}{N_h N_\theta} \sum_{N_h} \sum_{N_\theta} x^2(h, \theta, t)}$$

with $N_h$ the number of altitudes and $N_\theta$ the number of angles.

4. The method as claimed in claim 1, wherein the normalization of a temporal signal x(z,t) by means of said temporal function f(t) corresponds to the division of said temporal signal by said temporal function:

$$x_{norm}(z, t) = \frac{x(x, t)}{f(t)}.$$

5. The method as claimed in claim 1, wherein a temporal signal representing the amplitude of the sound propagated in the material as a function of time for a position of the receiving transducer is a A-type spatio-temporal representation representing the amplitude of the sound propagated in the material as a function of time for a position of the receiving transducer.

6. The method as claimed in claim 1, wherein the detection of the defects comprises a step of determination of at least one C-type spatial representation by selecting for each position of the ultrasonic receiving transducer the maximum value over time of the absolute value of the normalized temporal signal corresponding to this position.

7. The method as claimed in claim 6, wherein the detection of the defects comprises a step of spatial filtering of said at least one C-type spatial representation by means of a low-pass spatial filter.

8. The method as claimed claim 6, wherein the detection of the defects comprises a step of comparison with a detection threshold of the ratio of, on the one hand, the absolute value of the difference between the value taken by the C-type spatial representation for a position and the average of the values of the C-type spatial representation and on the other hand the standard deviation of the values of the C-type spatial representation.

9. The method as claimed in claim 1, wherein, prior to the determination of the temporal function:
- at least one C-type spatial representation is determined by selecting for each ultrasonic receiving transducer position the maximum value over time of the absolute value of the temporal signal corresponding to this position,
- a pre-processing bi-dimensional low-pass spatial filter is applied to this C-type spatial representation in order to obtain an average level of the structure noise at each measurement position,
- each temporal signal is divided by the average level of the structure noise at the measurement position with which said temporal signal is associated.

* * * * *